United States Patent [19]

Allen et al.

[11] Patent Number: 5,214,061
[45] Date of Patent: May 25, 1993

[54] METHOD OF USING P-ACYLAMINOPHENOXYCARBAMATES AND DERIVATIVES AS ANALGESICS

[75] Inventors: Richard C. Allen, Flemington; Raymond W. Kosley, Jr., Bridgewater; Bettina Spahl, Edison, all of N.J.

[73] Assignee: Hoechst-Roussel Pharmaceuticals Inc., Somerville, N.J.

[21] Appl. No.: 837,190

[22] Filed: Feb. 18, 1992

Related U.S. Application Data

[62] Division of Ser. No. 566,291, Jul. 30, 1990, Pat. No. 5,109,011.

[51] Int. Cl.$^5$ ................ A61K 31/44; A61K 31/415
[52] U.S. Cl. ................................ 514/354; 514/356; 514/399; 514/490; 514/482; 514/487; 514/488
[58] Field of Search ........... 514/354, 356, 399, 490, 514/482, 487, 488

[56] References Cited

U.S. PATENT DOCUMENTS 5,109,011  4/1992  Allen et al. .................... 514/354

FOREIGN PATENT DOCUMENTS 57-7459  1/1982  Japan .

OTHER PUBLICATIONS

Nippon Oyo Dobutsu Konchu Gakkai-Shi, vol. 12, No. 4, pp. 202-210 (1968).
Black et al., An Evaluation of Aminozectran and Carbofuran Derivatives as Mothproofers, J. Text. Int. No. 2, pp. 68-70 (1976).
CA 73(11):54978a (1968).
CA 84(20):137085k (1976).
CA 96(25):217485d (1982).
CA 96(25):217497j (1982).

*Primary Examiner*—Mary C. Lee
*Assistant Examiner*—Lenora Miltenberger
*Attorney, Agent, or Firm*—Elliott Korsen

[57] ABSTRACT

This invention relates to p-acylaminophenoxycarbamates having the formula

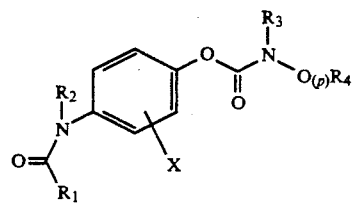

where $R_1$ and $R_2$ are each independently hydrogen, loweralkyl, aryl and arylloweralkyl; $R_3$ is hydrogen, loweralkyl, arylloweralkyl; $R_4$ is hydrogen, loweralkyl, formyl, alkylcarbonyl, arylloweralkyl, phenylcarbonyl, arylloweralkylcarbonyl, substituted phenylcarbonyl, pyridylcarbonyl, and substituted pyridylcarbonyl with the proviso that if $R_4$ contains a carbonyl group directly attached to the oxygen of the N-O moiety, $R_3$ cannot be hydrogen; or $R_3$ and $R_4$ taken together from a heterocyclic ring selected from the group consisting of imidazole or loweralkylimidazole; X is hydrogen, halogen, hydroxy, loweralkyl, loweralkoxy, nitro, amino or trifluoromethyl; and p is an integer selected from 0 and 1; the pharmaceutically acceptable acid addition salts thereof, and where applicable, the geometric and stereoisomers and racemic mixtures thereof. The compounds of this invention display utility as analgesics.

1 Claim, No Drawings

METHOD OF USING P-ACYLAMINOPHENOXYCARBAMATES AND DERIVATIVES AS ANALGESICS

This is a division of application Ser. No. 566,291 filed Jul. 30, 1990 now U.S. Pat. No. 5,109,011.

This invention relates to compounds of the formula

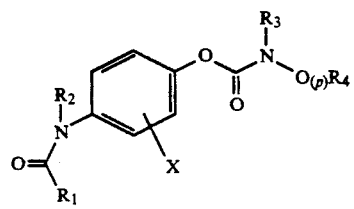
(I)

where $R_1$ and $R_2$ are each independently hydrogen, loweralkyl, aryl and arylloweralkyl; $R_3$ is hydrogen, loweralkyl, arylloweralkyl; $R_4$ is hydrogen, loweralkyl, formyl, alkylcarbonyl, arylloweralkyl, phenylcarbonyl, arylloweralkylcarbonyl, substituted phenylcarbonyl, pyridylcarbonyl, and substituted pyridylcarbonyl with the proviso that if $R_4$ contains a carbonyl group directly attached to the oxygen of the N-O moiety, $R_3$ cannot be hydrogen; or $R_3$ and $R_4$ taken together form a heterocyclic ring selected from the group consisting of imidazole or loweralkylimidazole; X is hydrogen, halogen, hydroxy, loweralkyl, loweralkoxy, nitro, amino or trifluoromethyl; and p is an integer selected from 0 and 1; the pharmaceutically acceptable acid addition salts thereof, and where applicable, the geometric and stereoisomers and racemic mixtures thereof.

Preferred embodiments of the invention are those substituents of Compound I where $R_1$ is selected from loweralkyl; $R_2$ is selected from hydrogen or methyl; $R_3$ is selected from loweralkyl or hydrogen; and $R_4$ is selected from hydrogen, loweralkyl, arylloweralkyl, alkylcarbonyl, pyridylcarbonyl, arylcarbonyl and p is 1.

Throughout the specification and appended claims, a given chemical formula or name shall encompass all geometric and stereoisomers and racemic mixtures where such isomers and mixtures exist.

The following definitions shall apply throughout the specification and the appended claims unless otherwise indicated.

The term "lower" means the group it is describing contains from 1 to 6 carbon atoms. The term "alkyl" refers to a straight or branched chain hydrogen containing no saturation, e.g., methyl, ethyl, propyl, isopropyl, t-butyl, neopentyl, n-hexyl, etc.; the term "arylloweralkyl" refers to a monovalent substituent which consists of an "aryl" group, e.g., phenyl, o-tolyl, m-methoxyphenol, etc., as defined by the formula

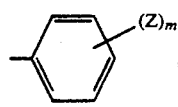

where Z and m are as defined below, linked through a loweralkyl group having its free valence bond from a carbon of the loweralkylene group, and having a formula

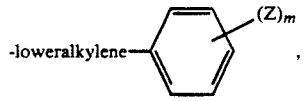

where Z is hydrogen, halogen, loweralkyl, loweralkoxy, $CF_3$, $NO_2$ and $NH_2$; and m is an integer of 1 to 3; such that the phenyl moiety can be substituted with up to three groups which can be the same or different; the term "alkylene" refers to a bivalent radical of the lower branched or unbranched alkyl group it is derived from having valence bonds from two terminal carbons thereof; e.g., ethylene ($-CH_3CH_2-$), propylene ($-CH_2CH_2CH_2-$), isopropylene

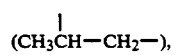

etc.; the term "alkoxy" refers to a monovalent substituent which consists of an alkyl group linked through an ether oxygen having its free valence bond from the ether oxygen, e.g., methoxy, ethoxy propoxy, butoxy, pentoxy, etc., and the term "halogen" refers to a member of the halogen family consisting of fluorine, chlorine, bromine and iodine.

The compounds of the present invention are prepared in the following manner. The substituents $R_1$, $R_2$, $R_3$, $R_4$, X and p are as defined above unless indicated otherwise.

An alkylamidophenol of the formula

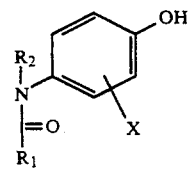
(II)

is reacted with a 1,1'-carbonyldiimidazole of the formula

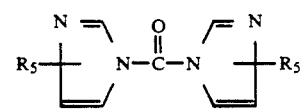

where $R_5$ is loweralkyl or hydrogen, to afford compound III of the invention of the formula

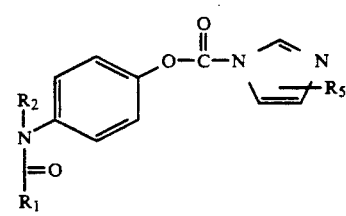
(III)

This reaction is typically carried out in an inert gas, e.g. nitrogen, etc. in an ethereal solvent, e.g., tetrahydrofuran, diethyl ether, dimethoxyether, etc., at a temperature of about $-10°$ C. to $60°$ C., preferably $15°$ to $30°$ C.

Compound III of the invention is reacted with an alkyl or arylhydroxylamine or its acid salt, preferably the hydrochloride, of the formula

where $R_3$ and $R_4$ are as previously defined, to afford Compound IV of the invention of the formula

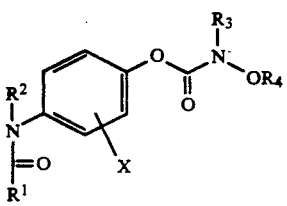

This standard substitution reaction typically takes place under an inert gas, e.g. nitrogen, in a polar aprotic solvent, e.g., dimethylformamide, dimethyl sulfoxide, etc., at a temperature of about 0° to 60° C., preferably from 10° to 40° C.

Compound IVa of the invention, where $R_3$ is hydrogen and $R_4$ is methyl phenyl ether, of the formula

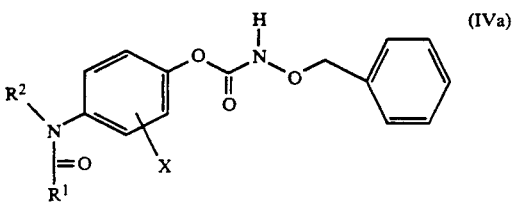

is alkylated, in a conventional manner, to afford Compound V of the invention of the formula

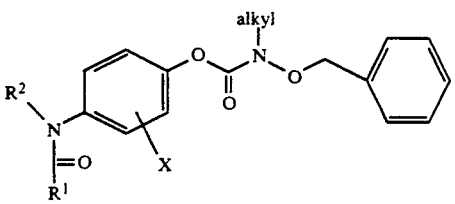

This reaction is exemplified in Olsen et al., *J. Org. Chem.* 46, 5438–5441 (1981), where methyl iodide is used as the alkylation agent.

Compound IVa or V of the invention is reduced to give Compound VI of the invention of the formula

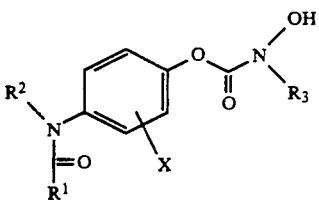

This reduction is carried out in a conventional manner, i.e., under hydrogen gas at 1–5 atmospheres, preferably one atmosphere, in the presence of a metal catalyst, preferably, 10% palladium on carbon and in the presence of a suitable solvent, i.e., a loweralkanol, e.g., methanol, ethanol, etc. at a temperature of about 0° to 50° C. preferably 15° to 30° C.

Compound VI of the invention is actylated to give Compound VII of the invention of the formula

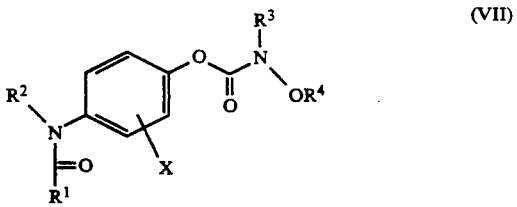

where $OR^4$ is alkylcarbonyloxy or arylcarbonyloxy.

Typically, this acylation reaction is carried out using an acid anhydride of the formula $(RCO)_2O$ where R is alkyl or aryl, as previously defined, with a base, e.g., triethylamine, pyridine, etc. in a solvent, i.e., tetrahydrofuran, at a temperature of about −20° to 50° C., preferably from −10° to 25° C.

Alternatively, Compound VII can be prepared by the reaction of Compound VI with an acyl chloride e.g., benzoyl chloride, isonicotinoyl chloride of the formula RCOCl, where R is alkyl or aryl, in the presence of a base, e.g., pyridine, triethylamine, etc. in an appropriate solvent, e.g., tetrahydrofuran, dimethylformamide, diethyl ether, etc., at a temperature of about −20° to 50° C., preferably −10° to 30° C.

The compounds of Formula (I) of the present invention are useful as analgesic agents due to their ability to alleviate pain in mammals as demonstrated in the phenyl-para-quinone writhing assay in mice, a standard assay for analgesia [Proc. Soc. Exptl. Biol. Med., 95,729 (1957)]. Presented in Table I is the analgesic effect of some of the compounds of the invention expressed as the oral dose at which 50% of the phenyl-para-quinone induced writhing is inhibited in the animals, i.e., the $ED_{50}$ value.

TABLE I

| Compound | Analgesic Activity $ED_{50}$ mg/kg |
|---|---|
| 4-(acetylamino)phenyl-N-hydroxy-N-methyl carbamate | 32.3 |
| 4-(acetylamino)phenyl-N-(acetyloxy)-N-methyl carbamate | 42.7 |
| 4-(acetylamino)phenyl-N-benzyloxy-N-methyl carbamate | 28.5 |
| Acetaminophen (standard) | 33.8 |

The analgesic relief of pain is achieved when the present compounds are administered to a subject requiring such treatment as an effective oral, parenteral or intravenous dose of from 0.01 to 100 mg/kg of body weight per day. A preferred effective dose within this usage is 10 to 50 mg/kg of body weight per day. It is to be understood however, that for any particular subject, specific dosage regimens should be adjusted according to the individual need and the professional judgment of the person administering or supervising the administration of the aforesaid compound. It is further understood that the dosages set forth herein are exemplary only and that they do not, to any extent, limit the scope or practice of the invention.

Effective amounts of the compounds of the invention may be administered to a subject by any one of various methods, for example, orally as in capsules or tablets, parenterally in the form of sterile solutions or suspensions, and in some cases intravenously in the form of sterile solutions. The compounds, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, malic, fumaric and oxalic acids.

The active compounds of the present invention may be administered orally, for example, with an inert diluent or with an edible carrier. They may be enclosed in gelatin capsules or compressed into tablets. For the purpose of oral therapeutic administration, these compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of active compound in such composition is such that a suitable dosage will be obtained. Preferred compositions and preparations according to the present invention are prepared so that an oral dosage unit form contains between 0.1 and 300 milligrams of the active compound.

The tablets, pills, capsules, troches and the like may also contain the following ingredients: a binder such as microcrystalline cellulose, gum tragacanth or gelatin; an excipient such as starch or lactose; a disintegrating agent such as alginic acid, Primogel ™, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate or orange flavoring. When the dosage unit form is a capsule, it may contain, in addition to materials of the above type, a liquid carrier such as fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose and/or other sweetening agents, preservatives, dyes, coloring agents and/or flavorings. Materials used in preparing these various compositions should be pharmaceutically pure and non-toxic in the amounts used.

For the purpose of parenteral therapeutic administration, the active compounds of this invention may be incorporated into a solution or suspension. These preparations should contain at least 0.1% of active compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascobic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:
3-(Acetylamino)phenyl-[1H-4-methyl-imidazol]-1-carboxylate;
4-(Propionylamino)phenyl-N-(benzyloxy) carbamate;
4-(Propionylamino)phenyl-N-(hydroxy) carbamate;
4-(Propionylamino)phenyl-N-(methyl)-N-(benzyloxy)-carbamate;
4-[N-(Propionyl)-N-methyl]amino]phenyl-N-(methyl)-N-(benzyloxy) carbamate;
4-(Propionylamino)phenyl-N-hydroxy-N-methyl carbamate;
4-(Propionylamino)phenyl-N-(acetyloxy)-N-methyl carbamate;
4-(Propionylamino)phenyl-N-methyl-N-[(pyridin-4-carbonyl]oxy] carbamate;
[4-(Acetylamino)-3-chloro]phenyl-N-hydroxy-N-methyl carbamate;
[4-(Acetylamino)-3-chloro]phenyl-N-(acetyloxy)-N-methyl carbamate;
[4-(Acetylamino)-3-chloro]phenyl-N-methyl-N-[[(pyridine-4-yl)carbonyl]oxy] carbamate;
4-(Acetylamino)-phenyl-N-methyl-N-[[(tetrahydrofuran-2-yl)carbonyl]oxy] carbamate;
4-(Acetylamino)-phenyl-N-ethyl-N-[[(pyridine-4-yl)carbonyl]oxy] carbamate;
4-[[(N-Acetyl)-N-(methyl)]-amino]phenyl-N-(acetyloxy)-N-methyl carbamate; and
4-(Formylamino)phenyl-N-(acetyloxy)-N-methyl carbamate.

EXAMPLES

The following examples are for illustrative purposes only and are not to be construed as limiting the invention. All temperatures are given in degrees centrigrade unless indicated otherwise.

EXAMPLE 1

4-(Acetylamino)phenyl-1H-imidazole-1-carboxylate

To a stirred solution of 25.0 g of 4-acetamidophenol dissolved in 1000 ml of tetrahydrofuran (THF hereafter) was added 42.9 g of 1,1'-carbonyldiimidazole. The mixture was stirred at room temperature under nitrogen for 18 hours. The resulting suspension was then filtered using vacuum filtration and rinsed with ethyl acetate. The residue was first dried under high vacuum at room temperature and then at 60° C. for 1½ hours to afford 16.6 g of 4-(acetylamino)phenyl-1H-imidazole-1-carboxylate, m.p. 174°-175° C.

ANALYSIS: Calculated for $C_{12}H_{11}N_3O_3$: 58.83% C; 4.52% H; 17.15% N. Found: 58.71% C; 4.50% H; 17.20% N.

EXAMPLE 2

4(Acetylamino)phenyl-N-(benzyloxy) carbamate

To 10.0 g of 4-(acetylamino)phenyl 1H-imidazole-1-carboxylate and 6.52 g of O-benzylhydroxylamine hydrochloride was added 100 ml of dry dimethylformamide (DMF hereafter). The solution was stirred at room temperature under nitrogen for 20 hours. The solution was then cooled in an ice bath. The cold solution was poured into a mixture of 600 ml ice/water, 400 ml of 5%

HCl and 1000 ml of ether. A solid crystallized from the ether layer. The solid was filtered and the filtrate was returned to the separatory funnel. The layers were separated. The ether layer was washed with saturated NaCl. The layers were separated again. The original HCl layer was extracted with ether. The ether layer was washed with saturated NaCl. The ether extracts were combined and concentrated. The residue was washed with ether and dried under high vacuum at room temperature for 30 minutes to provide 9.26 g of material. The material was recrystallized from cyclohexane/ethyl acetate and further purified by flash chromatography. The column the solvent removed to give a solid which was crystallized from cyclohexane/ethyl acetate and dried to give 4.19 g of 4-(acetylamino)phenyl-N-(phenylmethoxy) carbamate.

ANALYSIS: Calculated for $C_{16}H_{16}N_2O_4$: 64.00% C; 5.37% H; 9.32% N. Found: 64.03% C; 5.44% H; 9.33% N.

EXAMPLE 3

4-(Acetylamino)phenyl-N-hydroxy carbamate

To 1.17 g of 10% Pd on C was added a solution of 11.1 g of 4-(acetylamino)phenyl-N-(phenylmethoxy) carbamate in methanol (200 ml). The reaction mixture was stirred under $H_2$ (1 atmosphere) for 12 hours. The reaction mixture was filtered and the filtrate was concentrated. Flash chromatography was used to purify the product employing 5% $THF:CH_2Cl_2$. The product-containing fractions were combined and concentrated to provide a residue which was recrystallized from isopropyl alcohol/ether and dried at 60° C. for 2 hours to provide 0.61 g of 4-(acetylamino)phenyl-N-hydroxy carbamate, m.p. 173° C.

ANALYSIS: Calculated for $C_9H_{10}N_2O_4$: 51.43% C; 4.79% H; 13.32% N. Found: 51.26% C; 4.83% H; 13.23% N.

EXAMPLE 4

4-[N-(Acetyl)-N-(methyl)amino]phenyl-N-methyl-N-(benzyloxy) carbamate

To a solution of 15.0 g of 4-(acetylamino)phenyl-N-(benzyloxy) carbamate in 100 ml of THF at 0° C. was added 4.73 g of 80% NaH in mineral oil and 9.33 g of $CH_3I$. The reaction mixture was stirred at 0° C. for 1 hour and at room temperature for 48 hours. The reaction mixture was quenched by careful dropwise addition of water and then poured into a mixture of ice/water/chloroform, extracted with chloroform, washed with water, $Na_2S_2O_3$, dried with $Na_2SO_4$ and concentrated. The oil was purified by flash chromatography, employing 15% ethyl acetate/hexane. The product-containing fractions were combined and concentrated. The oil was crystallized from ether and the residue dried at 80° C. for 2 hrs. to provide 0.554 g of 4-[N-(Acetyl)-N-(methyl)amino]-phenyl-N-methyl-N-(benzyloxy) carbamate, m.p. 69°-71° C.

Analysis: Calculated for $C_{18}H_{20}N_2O_4$: 65.84% C; 6.14% H; 8.53% N. Found: 65.58% C; 6.09% H; 8.47% N.

EXAMPLE 5

4-(Acetylamino)phenyl-N-methyl-N-benzyloxy carbamate

To a solution of 12.6 g of 4-(acetylamino)phenyl-1H-imidazole-1-carboxylate and 8.9 g of O-benzyl-N-methylhydroxylamine hydrochloride in 125 ml of DMF was added 0.35 g of imidazole. The solution was stirred for 24 hours at room temperature under $N_2$. The reaction mixture was then poured into a mixture of ice/water/5% HCl/ethyl acetate. A precipitate formed, which was filtered off. The filtrate was returned to the separatory funnel and the organic layer separated, washed with water and saturated NaCl, dried with $Na_2SO_4$, filtered and concentrated. The residue was purified by flash chromatography employing 5% THF/methylene chloride to provide 2.46 g of product. The filtered precipitate was dried at 80° C. for 2 hours to provide 7.2 g of 4-(acetylamino)phenyl-N-methyl-N-benzyloxy carbamate, m.p. 143°-145° C.

Analysis: Calculated for $C_{17}H_{18}N_2O_4$: 64.96% C; 5.77% H; 8.91% N. Found: 65.17% C; 5.85% H; 8.80% N.

EXAMPLE 6

4-(Acetylamino)phenyl-N-hydroxy-N-methyl carbamate

To 2.00 g of 10% Pd/C was added a solution of 20.00 g of 4-(acetylamino)phenyl-N-methyl-N-benzyloxy carbamate in 500 ml of methanol. The reaction mixture was stirred under $H_2$ (1 atmosphere) at room temperature for 10 hours. The reaction mixture was filtered, and the filtrate concentrated. The residue was recrystallized from ethanol and the crystallized product dried at 80° C. for 3 hours to provide 7.42 g of 4-(acetylamino)phenyl-N-hydroxy-N-methyl carbamate, m.p. 196°-197° C.

Analysis: Calculated for $C_{10}H_{12}N_2O_4$: 53.57% C; 5.39% H; 12.49% N. Found: 53.41% C; 5.32% H; 12.43% N.

EXAMPLE 7

4-(Acetylamino)phenyl-N-(acetyloxy)-N-methyl carbamate

To 6.22 g of 4-(acetylamino)phenyl-N-hydroxy-N-methyl carbamate in 90 ml of THF at 0° C. was added 3.87 ml of triethylamine, and 2.62 ml of acetic anhydride. The reaction mixture was stirred at 0° C. for 3 hours. It was then poured into a mixture of ice/water/5% $HCl/CH_2Cl_2$ extracted with $CH_2Cl_2$, washed with water, saturated NaCl, dried with $Na_2SO_4$, filtered and concentrated. The residue as triturated with ether, the ether suspension filtered and the residue dried at 80° C. for 3 hours to provide 6.35 g of 4-(acetylamino)phenyl-N-(acetyloxy)-N-methyl carbamate, m.p. 111°-112° C.

Analysis: Calculated for $C_{12}H_{14}N_2O_5$: 54.13% C; 5.30% H; 10.52% N. Found: 54.01% C; 5.33% H; 10.46% N.

EXAMPLE 8

4-(Acetylamino)phenyl-N-(benzyloxy)-N-methyl carbamate

To 3.00 g of 4-(acetylamino)phenyl-N-hydroxy-N-methyl carbamate in 50 ml of THF was added 1.08 ml of pyridine and 1.55 ml of benzoyl chloride at 0° C. The reaction mixture was stirred for 3 hours poured into a mixture of ice/water/5% $HCl/CH_2Cl_2$, extracted with $CH_2Cl_2$, washed with water, saturated NaCl, dried with $Na_2SO_4$, filtered, and concentrated. The residue was purified by flash chromatography, employing 40% ethyl acetate/hexane. The product-containing fractions were combined and concentrated, and the residue dried at 80° C. for 2 hours to provide 3.54 g of 4-

(acetylamino)phenyl-N-(benzyloxy)-N-methyl carbamate, m.p. 109°-110° C.

Analysis: Calculated for $C_{17}H_{16}N_2O_5$: 62.19% C; 4.91% H; 8.53% N. Found: 61.98% C; 4.98% H; 8.46% N.

EXAMPLE 9

4-(Acetylamino)phenyl-N-methyl-N-[(4-pyridinylcarbonyl)oxy] carbamate

To 6.29 g of 4-(acetylamino)phenyl-N-hydroxy-N-methyl carbamate in 60 ml of DMF was added 7.8 ml of triethylamine and 5.11 g of isonicotinoyl chloride hydrochloride. The reaction mixture was stirred for 24 hours at room temperature under $N_2$. To the reaction mixture was added an additional 3.9 ml of triethylamine and 2.11 g of isonicotinoyl chloride HCl, after which the reaction mixture was again stirred for 24 hours under $N_2$. The mixture was then poured into ice-/saturated $NaHCO_3/CH_2Cl_2$, extracted with $CH_2Cl_2$ washed with water, saturated NaCl, dried with $Na_2SO_4$, filtered and concentrated. The residue was purified by flash chromatography, employing 5% $THF/CH_2Cl_2$, and the product-containing fractions combined and concentrated. The impure fractions were combined and recrystallized from ethanol/ether. The product was dried at 80° C. for 2 hours to provide 3.96 g of 4-(acetylamino)phenyl-N-methyl-N-[(4-pyridinylcarbonyl)oxy] carbamate, m.p. 165°-166°.

Analysis: Calculated for $C_{16}H_{15}N_3O_5$: 58.36% C; 4.59% H; 12.76% N. Found: 58.24% C; 4.55% H; 12.65% N.

We claim:

1. A method of alleviating pain in a mammal which comprises administering to a mammal a pain alleviating effective amount of a compound of the formula

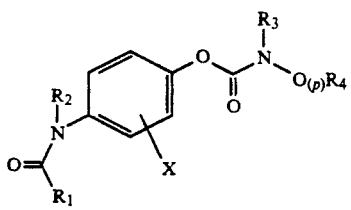

where $R_1$ and $R_2$ are each independently hydrogen, loweralkyl, aryl or arylloweralkyl; $R_3$ is hydrogen, loweralkyl or arylloweralkyl; $R_4$ is formyl, alkylcarbonyl, arylloweralkyl, phenylcarbonyl, arylloweralkylcarbonyl, substituted phenylcarbonyl, pyridylcarbonyl or substituted pyridylcarbonyl with the proviso that if $R_4$ contains a carbonyl group directly attached to the oxygen of the N-O moiety, $R_3$ cannot be hydrogen; or $R_3$ and $R_4$ taken together from a heterocyclic ring selected from the group consisting of imidazole or loweralkylimidazole; the substituents on the substituted phenyl- or substituted pyridylcarbonyl being 1 to 3 of the group selected from hydrogen, halogen, loweralkyl, loweralkoxy, $CF_3$, $NO_2$ or $NH_2$; X is hydrogen, halogen, loweralkyl, nitro, amino or trifluoromethyl; and p is an integer selected from 0 and 1; or a pharmaceutically acceptable acid addition salt thereof, or where applicable, a geometric or stereoisomer or racemic mixture thereof.

* * * * *